United States Patent
Steuer et al.

(10) Patent No.: US 6,746,415 B1
(45) Date of Patent: Jun. 8, 2004

(54) METHOD OF BLOOD CONSTITUENT MONITORING USING IMPROVED DISPOSABLE EXTRACORPOREAL CONDUIT

(75) Inventors: Robert R. Steuer, Pleasant View, VT (US); David R. Miller, Morgan, VT (US)

(73) Assignee: Hema Metrics, Inc., Kaysville, UT (US)

( * ) Notice: Subject to any disclaimer, the term of this patent is extended or adjusted under 35 U.S.C. 154(b) by 0 days.

(21) Appl. No.: 09/577,944

(22) Filed: May 25, 2000

Related U.S. Application Data (62) Division of application No. 08/955,989, filed on Oct. 22, 1997, now Pat. No. 6,090,061.
(60) Provisional application No. 60/029,586, filed on Oct. 23, 1996.

(51) Int. Cl.[7] .................. A61M 37/00; C02F 1/44; B01D 33/82
(52) U.S. Cl. .................. 604/4.01; 210/645; 210/97
(58) Field of Search .................. 210/103, 97, 645–646; 73/861.18; 604/4.01, 5.01

(56) References Cited

U.S. PATENT DOCUMENTS

| | | | |
|---|---|---|---|
| 5,066,859 A | * 11/1991 | Karkar et al. | 250/339.09 |
| 5,101,825 A | * 4/1992 | Gravenstein et al. | 128/633 |
| 5,111,817 A | * 5/1992 | Clark et al. | 128/633 |
| 5,158,091 A | * 10/1992 | Butterfield et al. | 128/672 |
| 5,230,341 A | * 7/1993 | Polaschegg | 600/481 |
| 5,237,999 A | * 8/1993 | von Berg | 128/673 |
| 5,456,253 A | * 10/1995 | Steuer et al. | 128/633 |
| 5,685,989 A | * 11/1997 | Krivitski et al. | 210/103 |

* cited by examiner

*Primary Examiner*—Angela D. Sykes
*Assistant Examiner*—Leslie R. Deak
(74) *Attorney, Agent, or Firm*—Jacobson Holman PLLC (57) ABSTRACT

A cuvette having a pedestal for transmitting light through a relatively thin layer of blood. While the pedestal enables the use of a small path length it also permits the use of a high volume and/or high flow rate conduit. The pedestal further enables methods of determining various blood parameters in which the path length, d, is fixed; i.e., there are little or no pulsatile variations. Hence, the flow-through cuvette accommodates a large range of blood flow rates without any reduction in accuracy of the hematocrit measurement. The pedestal, because of its elliptical shape, does not damage or hemolyze the individual red blood cells as they pass through. A quantitative method for determining changes in blood volume in view of the path length is provided along with a method for measuring a patient's cardiac output and oxygen consumption rate. Cardiac output is obtained by injecting a saline arterial bolus and a saline venous bolus into a patient and measuring the change in hematocrit caused by each bolus. The oxygen consumption rate is then determined using the cardiac output and measuring the degree of oxygen saturation.

Finally, an improved cuvette and corresponding method of measuring microemboli is provided. The cuvette contains multiple mini-lenses that focus narrow beams of light through the blood. These narrow beams of light are individually monitored by detectors.

4 Claims, 7 Drawing Sheets

METHOD OF BLOOD CONSTITUENT MONITORING USING IMPROVED DISPOSABLE EXTRACORPOREAL CONDUIT

CROSS REFERENCE TO RELATED APPLICATION

This is a divisional of application Ser. No. 08/955,989 filed on Oct. 22, 1997 Now U.S. Pat. No. 6,090,06 which in turn claims priority to U.S. provision applcation Ser. No. 60/029,586, filed Oct. 23, 1996.

BACKGROUND

1. Field of the Invention

The present invention is directed to an improved extracorporeal conduit and methods and systems for deriving desired biologic constituent concentration values present in a flowing fluid.

2. Background

Medical professionals routinely desire to know the hematocrit, oxygen saturation, and oxygen consumption rate of a patient. Especially in critically ill patients or in cardiovascular surgery, the oxygen consumption rate, hematocrit value and microemboli content become very significant parameters.

The prior art contains disclosures of flow-through cuvettes that may be used in a blood conduit for the spectrophotometric analysis of blood. For example, U.S. Pat. No. 5,456,253 discloses a disposable conduit/cuvette for analyzing blood.

OBJECTS OF THE INVENTION

It is an object of the present invention to provide systems and methods for noninvasively and continuously monitoring such biologic constituents as the percent blood volume change, hematocrit, oxygen saturation, oxygen consumption rate, and microemboli content during such treatment/ procedures as hemodialysis or cardiovascular surgery.

It is another object of the present invention to monitor the above mentioned parameters without incurring instabilities, inaccuracies, and the need for recalibration as required in the presently known reflective and transmissive photometric techniques.

Another object of the present invention is to measure hematocrit, blood volume, oxygen saturation, oxygen consumption rate, microemboli, and cardiac output and visually display their corresponding values in real-time.

It is still another object of the present invention to provide systems and methods that are easy to use, save nursing staff time, and operate noninvasively and economically.

Another object of the present invention is to provide a cuvette which may be used in spectrophotometric determinations of desired biologic constituent concentration values of a fluid passing through this cuvette accommodating a large range of flow rates.

Another object of the present invention is to provide in this fluid-channeling cuvette a means by which the detection of the above mentioned parameters are unaffected by large variations in flow rates and are likewise unaffected by large variations in oxygen saturation such that the computation of blood constituent and blood flow parameters, including cardiac output, may be easily accomplished.

It is a further object of the present invention to provide a flow-through cuvette having a fixed, small path length.

These and other objects are achieved by the methods and apparati of the present invention.

SUMMARY OF THE INVENTION

The present invention provides a cuvette having a pedestal for transmitting light through a relatively thin layer of blood. While the pedestal enables the use of a small path length it also permits the use of a high volume and/or high flow rate conduit. Because the pedestal is situated within a large volume cuvette, the blood pressure within the cuvette remains low. The pedestal further enables methods of determining various blood parameters in which the path length, d, is fixed; i.e., there are little or no pulsatile variations.

The ability to change the internal and external dimensions of the blood chamber to accommodate for very large blood flows is important, especially with flow rates of 100 ml/min to 7,000 ml/min used in cardiovascular surgery. Hence, the flow-through cuvette of the present invention accommodates a large range of blood flow rates without any reduction in accuracy of the hematocrit measurement. The pedestal in the cuvette of the present invention because of its elliptical shape does not damage or hemolyze the individual red blood cells as they pass through.

The present invention further provides a quantitative method for determining changes in blood volume in view of the path length.

The present invention also provides a method for measuring a patient's cardiac output and oxygen consumption rate. Cardiac output is obtained by injecting a saline arterial bolus and a saline venous bolus into a patient and measuring the change in hematocrit caused by each bolus. The oxygen consumption rate is then determined using the cardiac output and measuring the degree of oxygen saturation.

The present invention further provides an improved cuvette and corresponding method of measuring microemboli. The cuvette contains multiple mini-lenses that focus narrow beams of light through the blood. These narrow beams of light are individually monitored by detectors. When a microemboli, such as platelet aggregates, clots, air bubbles, etc. pass through a beam, a "spike" is recorded by a detector. The amplitude and width of spikes provides information on the size of microemboli and the spike frequency provides information on the concentration of microemboli.

DETAILED DESCRIPTION OF THE INVENTION

In preferred embodiments, measurements are conducted using the apparatus (or modified versions thereof) described in U.S. Pat. Nos. 5,456,253 and 5,372,136, which are incorporated herein as if reproduced in full below. Both of these patents are intended to form part of the present disclosure. It should be understood that the improvements and modifications of the present invention can be applied to a wide variety of blood monitoring apparati and, thus, are not limited to certain preferred embodiments such as the above-cited U.S. patents.

Figure 1:
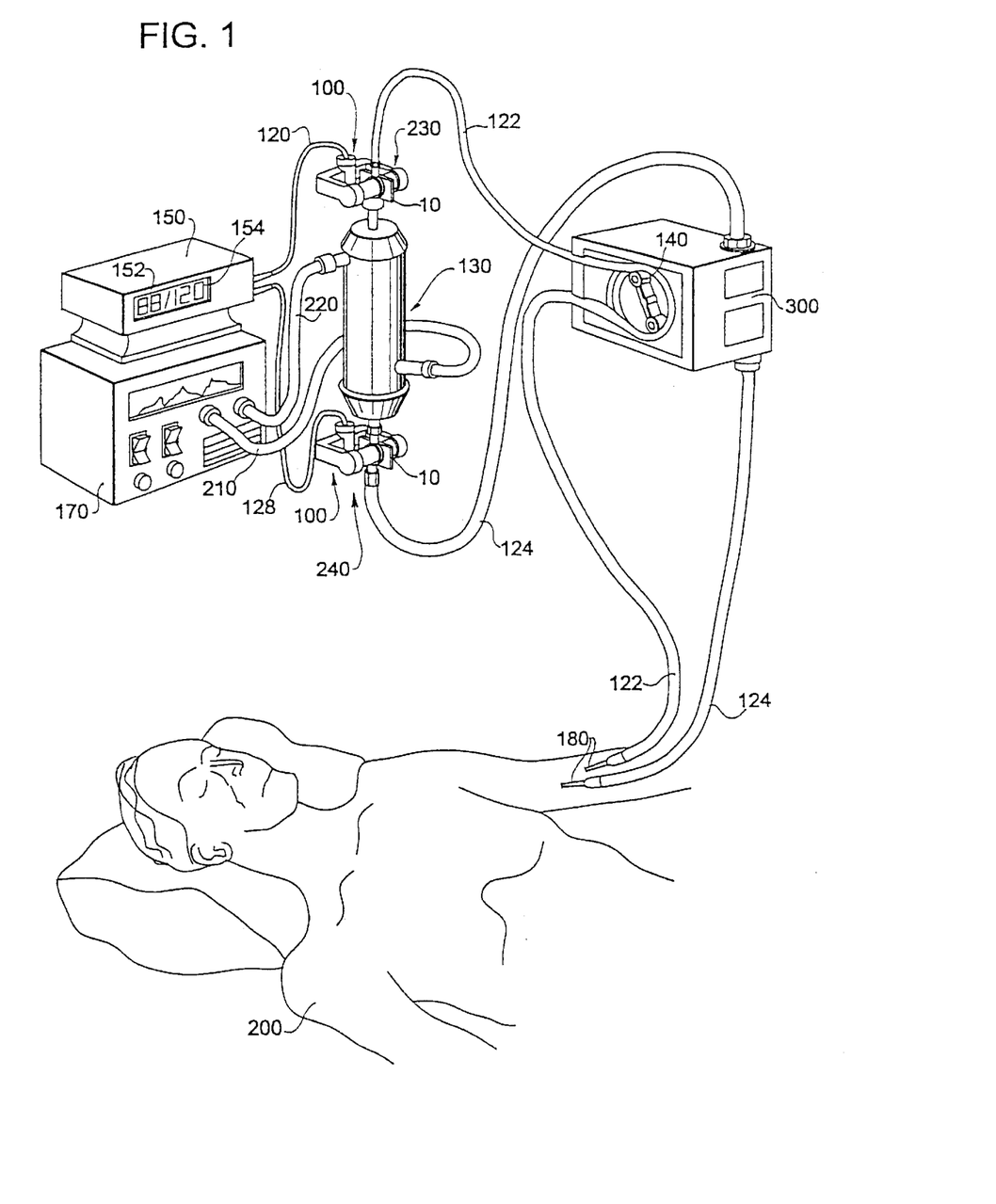
FIG. 1 shows a typical hemodialysis tubing circuit and connections.

FIG. 1 shows a typical hemodialysis tubing circuit and apparati that may be used in the present invention. The numbered components in FIG. 1 are the same as in the corresponding Figure of U.S. Pat. No. 5,456,253.

In hemodialysis, blood is taken out of a patient 200 by an intake catheter means, one example of which is shown in FIG. 1 as an input catheter 122. Input catheter 122 is intravenously inserted into patient 200 at a site 180 and is used for defining a blood passageway upstream of a blood filter used to filter the impurities out of the blood. The blood filter is also called a dialyzer 130. The unclean blood flows from an artery in patient 200 to a pump means, an example of which is pump 140. From pump 140, the blood flows to dialyzer 130. Dialyzer 130 has an input port 230 and an output port 240. The pump 140 performs the function of moving the unclean blood from patient 200 into input port 230, through dialyzer 130, and out of dialyzer 130 at output port 240.

Specifically, unclean blood in input catheter 122 is transported to input port 230 of dialyzer 130. After passing through and being cleansed by dialyzer 130, the blood may receive further processing, such as heparin drip, in hemodialysis related component 300. The now clean blood is returned to patient 200 after the dialyzing process by means of an output catheter means, an example of which is output catheter 124. Output catheter 124, which is also intravenously inserted into patient 200 at site 180, defines a blood passageway which is downstream from dialyzer 130, taking the blood output by dialyzer 130 back to patient 200.

As mentioned, the hemodialysis process uses a blood filter or dialyzer 130 to clean the blood of patient 200. As blood passes through dialyzer 130, it travels in straw-like tubes (not shown) within dialyzer 130 which serve as membrane passageways for the unclean blood. The straw-like tubes remove poisons and excess fluids through a process of diffusion. An example of excess fluid in unclean blood is water and an example of poisons in unclean blood are blood urea nitrogen (BUN) and potassium.

The excess fluids and poisons through an ultrafiltration process are removed by a clean dialysate liquid fluid, which is a solution of chemicals and water. Clean dialysate enters dialyzer 130 at an input tube 210 from a combined controller and tank 170. The dialysate surrounds the straw-like tubes in dialyzer 130 as the dialysate flows down through dialyzer 130. The clean dialysate picks up the excess fluids and poisons passing through the straw-like tubes, by diffusion, and then returns the excess fluids and poisons with the dialysate out of dialyzer 130 via an output tube 220, thus cleansing the blood. Dialysate exiting at output tube 220 after cleansing the blood may be discarded.

In some cases, unclean blood flows from an artery in patient 200 to pump 140 and then to dialyzer 130. Unclean blood flows into dialyzer 130 from input catheter 122 and clean blood flows out of dialyzer 130 via output catheter 124 back to patient 200.

Installed at either end of dialyzer 130 is a spectrophotometry means for defining a blood flow path, for emitting radiation into the blood in the flow path, and for detecting radiation passing through both the blood and the flow path. The spectrophotometry means includes a cuvette means 10 for defining the blood flow path, and an emitter/detector means 100 for emitting and detecting radiation. Within the emitter/detector means is both an emission means for directing radiation and a detector means for detecting radiation.

Figure 3:
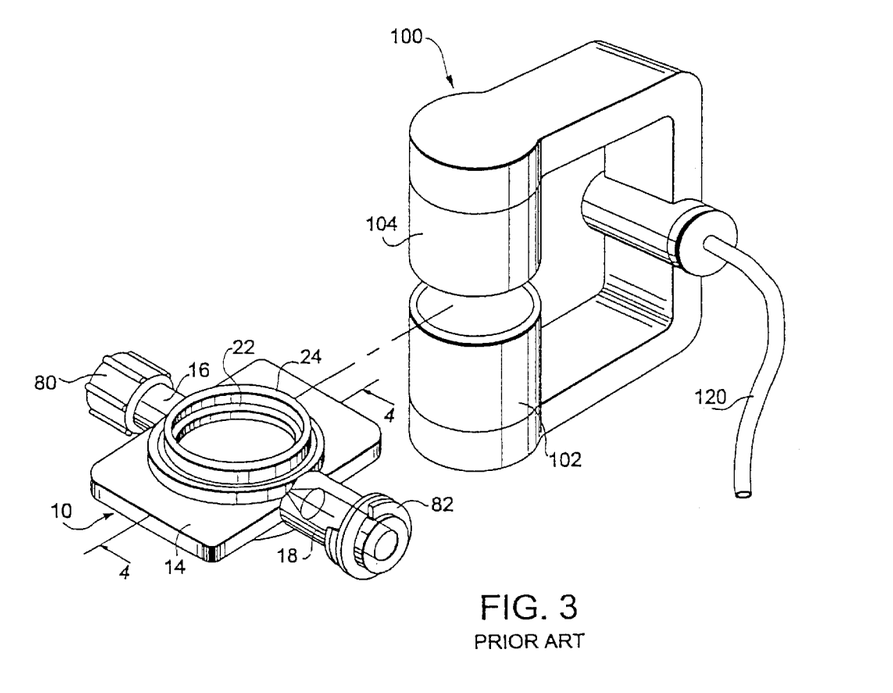
FIG. 3 shows a prior art flow-through cuvette.
Figure 4:
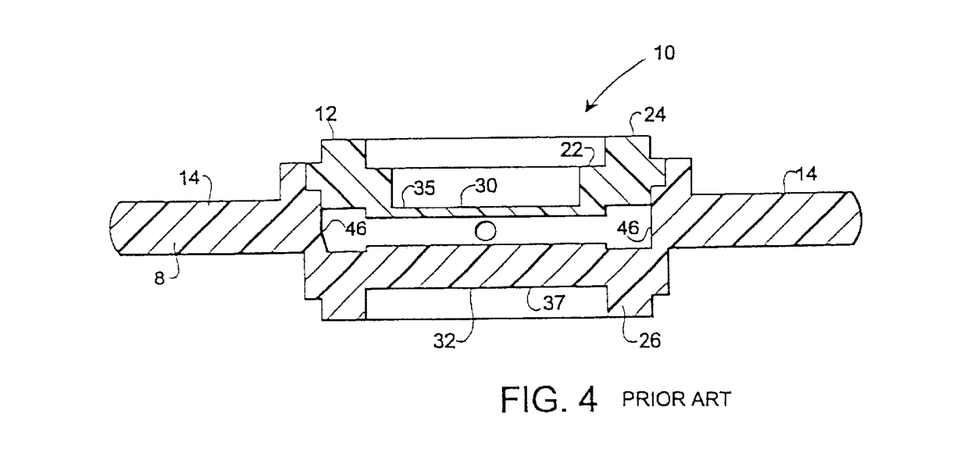
FIG. 4 shows a cross-section of the cuvette of FIG. 3.

In a prior art embodiment as shown in FIGS. 3 and 4, an example of the emitter/detector means is depicted by the emitter/detector apparatus 100. An example of the emission means is indicated by a photoemitter 102. Emitter/detector apparatus 100 also has a detection means, an example of which is depicted as a photodetector 104. An example of the cuvette means is shown in FIGS. 3 and 4 as cuvette 10.

Emitter/detector apparatus 100 enables the detection by photodetector 104 of the portion of radiation which is directed by photoemitter 102 to cuvette 10 and passes through both the blood therein and cuvette 10.

As shown in FIGS. 1 and 3, a cuvette 10 is installed at either end of dialyzer 130. Each cuvette 10 has a photoemitter 102 and a photodetector 104 thereon. In the preferred embodiment of the system, photoemitter 102 and photodetector 104 are shown as being held together by a spring loaded C-Clamp type in emitter/detector photo apparatus 100.

The emitter/detector means is electrically connected to a calculation means. In a preferred embodiment of the system, an example of the calculator means is depicted in FIG. 1 as computer 150 which is electrically connected to photoemitter 102 and photodetector 104 on emitter/detector apparatus 100 by means of cable 120 or 128.

Intake catheter 122 takes blood to cuvette 10 situated before input port 230 of dialyzer 130 by input 80. The blood passes through cuvette 10 and out of output 82 into dialyzer 130. Emitter/detector apparatus 100 at input port 230 of dialyzer 130 subjects the blood therein to wavelengths of electromagnetic radiation for the purposes of analysis, via spectrophotometry, so that the concentration of a desired biological constituent can be derived. Each photodetector 104, at both input port 230 and output port 240 of the dialyzer 130, communicates the detected radiation at least a first and a second wavelength via cable 120 or 128 to computer 150.

Computer 150 calculates both before dialysis and after dialysis concentrations of the sought-after or desired biologic constituent. Computer 150 then displays, respectively, at a first display 152 and a second display 154, the derived concentration of the biological constituent in either analogue or digital representations. The calculation means, shown here by example as computer 150, preferably has the multiple capability of simultaneous real-time computation and display of several blood parameters of interest.

Figure 2:
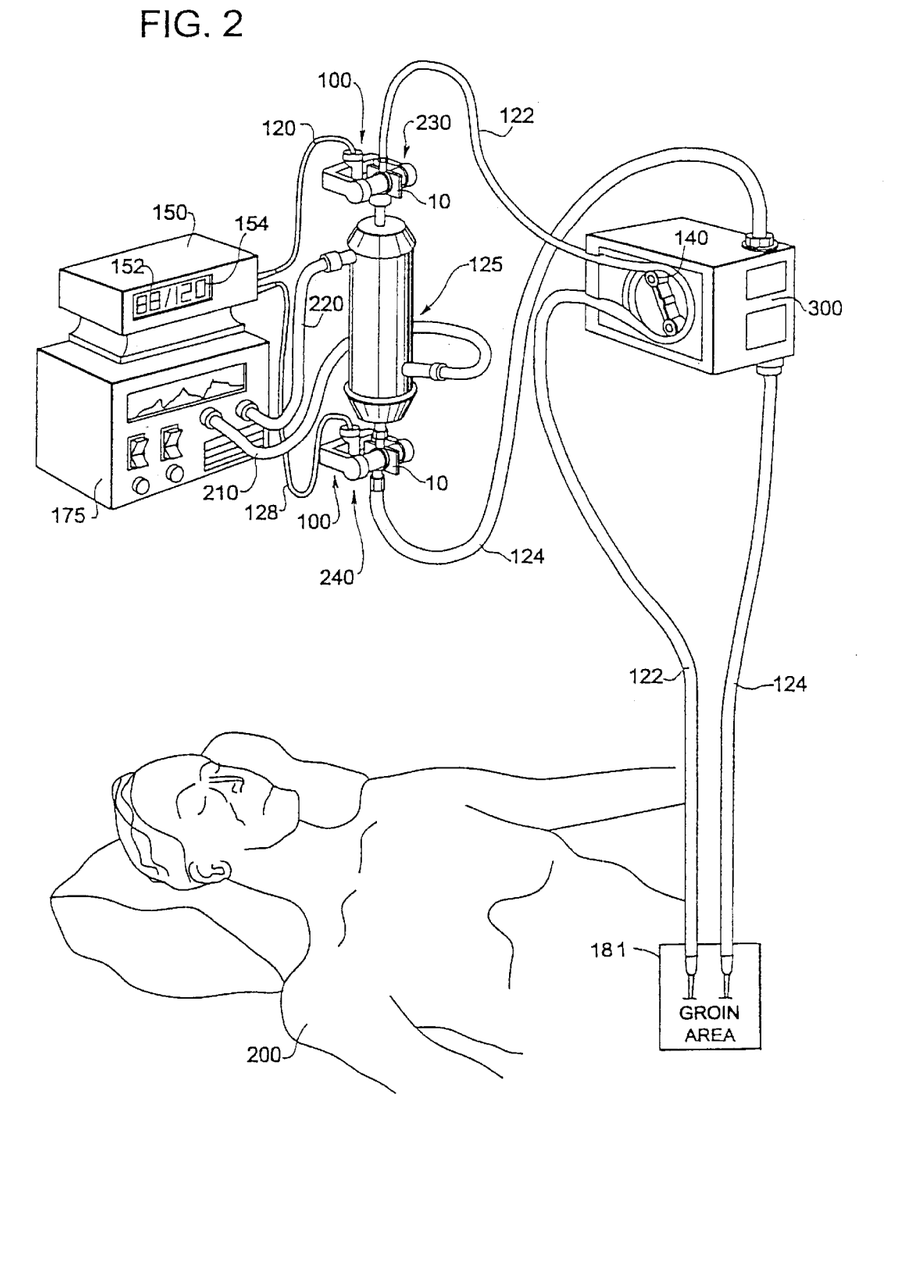
FIG. 2 shows a similar cardiovascular tubing circuit connection with disposable blood chambers in place.

FIG. 2 shows a similar system that is used during cardiovascular surgery. During cardiovascular surgery the site 181 at which blood is removed and returned is in the groin where the input catheter 122 is connected to the femoral vein and the output catheter 124 is connected to the femoral artery. Also, differing from the dialysis system, the withdrawn blood is oxygenated in an oxygenator 125 that is fed oxygen from oxygenator supply 175 through input tube 210.

A prior art cuvette 10 is shown in FIGS. 3 and 4. The inlet and the outlet to the cuvette are respectively indicated at 16 and 18, between which lies a cylindrical shaped portion of the cuvette 10, called herein the conduit.

As shown in FIG. 4, there is an upper housing assembly 12 which is assembled into lower housing assembly 8 so as to form cuvette 10. Upper housing assembly 12 can be installed to lower housing assembly 8 by means of an adhesive. Other and equivalent means such as friction welding or ultrasonic welding can also be employed. The purpose in properly sealing upper housing 12 to lower housing 8 is to create therebetween a fluid impervious and sealed attachment so that fluids conducted through cuvette 10 will not leak, seep, or wick-up at the points of connection between upper housing 12 and lower housing 8. The lower housing 8 has hand holds or wings 14 by which the cuvette 10 may be manually handled.

The conduit incorporates a transducer means. As stated, the transducer means varies the predetermined separation between the two opposed walls with each pressure pulsation in the fluid. In the presently preferred embodiment, an example of the transducer means is represented in FIGS. 3 and 4 as wall 30 which has an opposing wall 32 thereto.

The pulsatile flowing fluid flows in the conduit within the area bounded in between a vertical wall 46 and opposed walls 30 and 32.

Inlet 16 and outlet 18 are linearly aligned on either side of the conduit and share a common longitudinal axis passing therebetween. The cylindrical conduit between inlet 16 and outlet 18 has a longitudinal axis passing through opposing walls 30, 32 that are normal to the common longitudinal axis of inlet 16 and outlet 18. As shown in FIG. 4, opposing wall 30 is preferably thinner than opposing wall 32.

The outer surface 37 of opposing wall 32 in the conduit also has a means for receiving an emission means 102 that extends from the wall. The outer surface 35 of the opposed wall 30 has a means for receiving a detector means 104. In the presently preferred embodiment, the means for receiving a photodetector 104 is indicated in FIGS. 3 and 4 as the combination of the first ring-shaped surface 22 with a second ring-shaped surface 24, both of which extend from opposing wall 30. The two ring-shaped surfaces 22 and 24 are styled to accept cylindrical photodetector 104, shown in FIG. 3.

A means extends from the other one of the opposed walls for receiving a photoemitter means 102. In the presently preferred embodiment, the ring-shaped surface 26 is concentric to ring-shaped surfaces 22 and 24 and extends from opposing wall 32 so as to accept cylindrical photoemitter 102.

As to the cuvette 10, it is preferable that ring-shaped surfaces 22 and 24 are concentric to each other and are concentric with ring-shaped surface 26, and the ring-shaped surface 22 has a lesser inner diameter than ring-shaped surface 24.

The cuvette 10 is described in greater detail in previously incorporated U.S. Pat. No. 5,456,253 at column 8, line 33 through column 13, line 30 and FIGS. 2 through 10.

The path length d of light through the blood is the distance between the inner surface 33 of separation wall 32 and the inner surface 31 of separation wall 30.

The present invention provides an improvement in the cuvette-conduit system wherein a light-carrying pedestal 92 projects into the blood flow path of the cuvette. An embodiment of the inventive pedestal is illustrated in cross-section in FIG. 5, where like numerals denote like elements to the cuvette of FIGS. 3 and 4.

Figure 5:
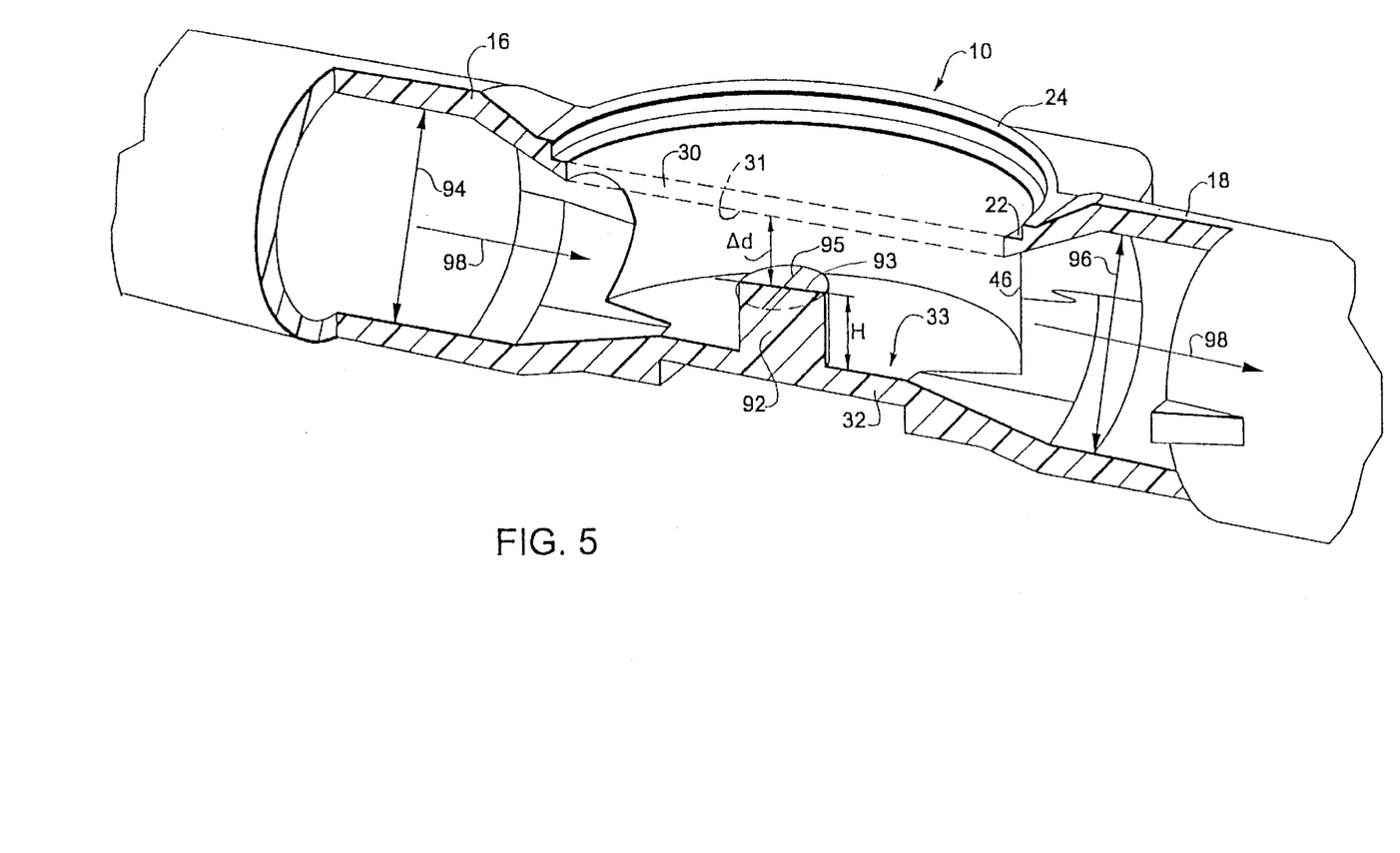
FIG. 5 shows a longitudinal cross section of the improved disposable blood conduit with a "pedestal" for effective light piping.

Incorporating a pedestal into a flow through cuvette 10 provides for a shorter path length with little or no pulsatile variation and allows for a large variation in flow rate and a large flow rate without leakage from the cuvette. As the change in path length, $\Delta d$, becomes small, $\Delta I/I$ becomes small, thus providing more accurate measurements of various blood constituents and blood flow parameters (see, e.g., U.S. Pat. No. 5,372,136). The pedestal of the present invention is a light conduit. The shorter path length created by the pedestal allows more light to reach the detector, especially at strongly absorbed wavelengths such as 660 nm, thus enabling more accurate spectrophotometric determinations.

While creating a shorter path length, the pedestal also allows the cuvette to have a large diameter 94 and 96, i.e., it increases the separation between the inner surface 33 of wall 32 and the inner surface 31 of wall 30. This decreases pressure inside the cuvette and prevents flow perturbations even when the flow rate is large.

Preferably the height H of the pedestal is selected such that the path length $\Delta d$ through the blood is between about 0.060 and 0.25 inches (0.15 and 0.64 cm) and the distance between walls 30 and 32 is between about 0.27 and 0.35 inches. In a preferred embodiment, the pedestal has a height of approximately 0.165 inches.

Figure 9:
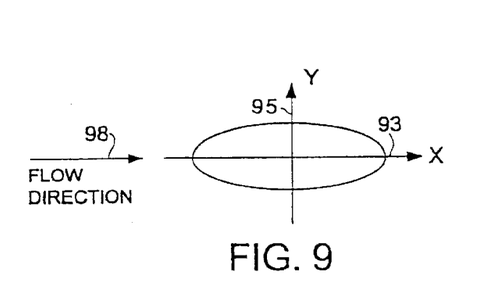
FIG. 9 is a schematic diagram of the top of the pedestal for the conduit of FIG. 5.

With reference to FIG. 9, the pedestal is preferably an elliptical cylinder with preferred elliptical measurements of 0.85 inches by 0.200 inches with the long or x-axis 93 of the ellipse parallel to the flow direction 98 and the short or y-axis 95 is transverse to the flow direction. Alternatively, the long axis of the pedestal is preferably about ⅛ the diameter of the interior of the cuvette. The pedestal is preferably made of a rigid material that is transparent to the wavelengths of interest. In a particularly preferred embodiment the pedestal is an elliptical cylindrically-shaped thin, rigid polymeric material formed integrally with separation wall 32. The ability to place a pedestal, as in FIG. 5, in the midst of a large diameter environment and not be concerned about variations in the blood thickness, d, is an important feature of the present invention. The d dimension cancels out as seen in the following formulae:

$$\text{since: } I_8 = I_{o8}(e^{-E_8 d}) \tag{1}$$

$$I_8 = I_{o8}(e^{-E_{13} d}) \tag{2}$$

$$\text{note: } \log(I/I_o)_8 = E_8 d \tag{3}$$

$$\log(I/I_o)_8 = E_{13} d \tag{4}$$

$$\text{and } (I/I_o)_8/\log(I/I_o)_{13} = E_8/E_{13} \tag{5}$$

The subscripts 8 and 13 represent wavelengths of 810 nm and 1300 nm, respectively, and E is the extinction coefficient.

Thus the hematocrit and blood volume change are non-invasively derived by utilizing this electromagnetic radiation as the information carrier.

Figure 6:
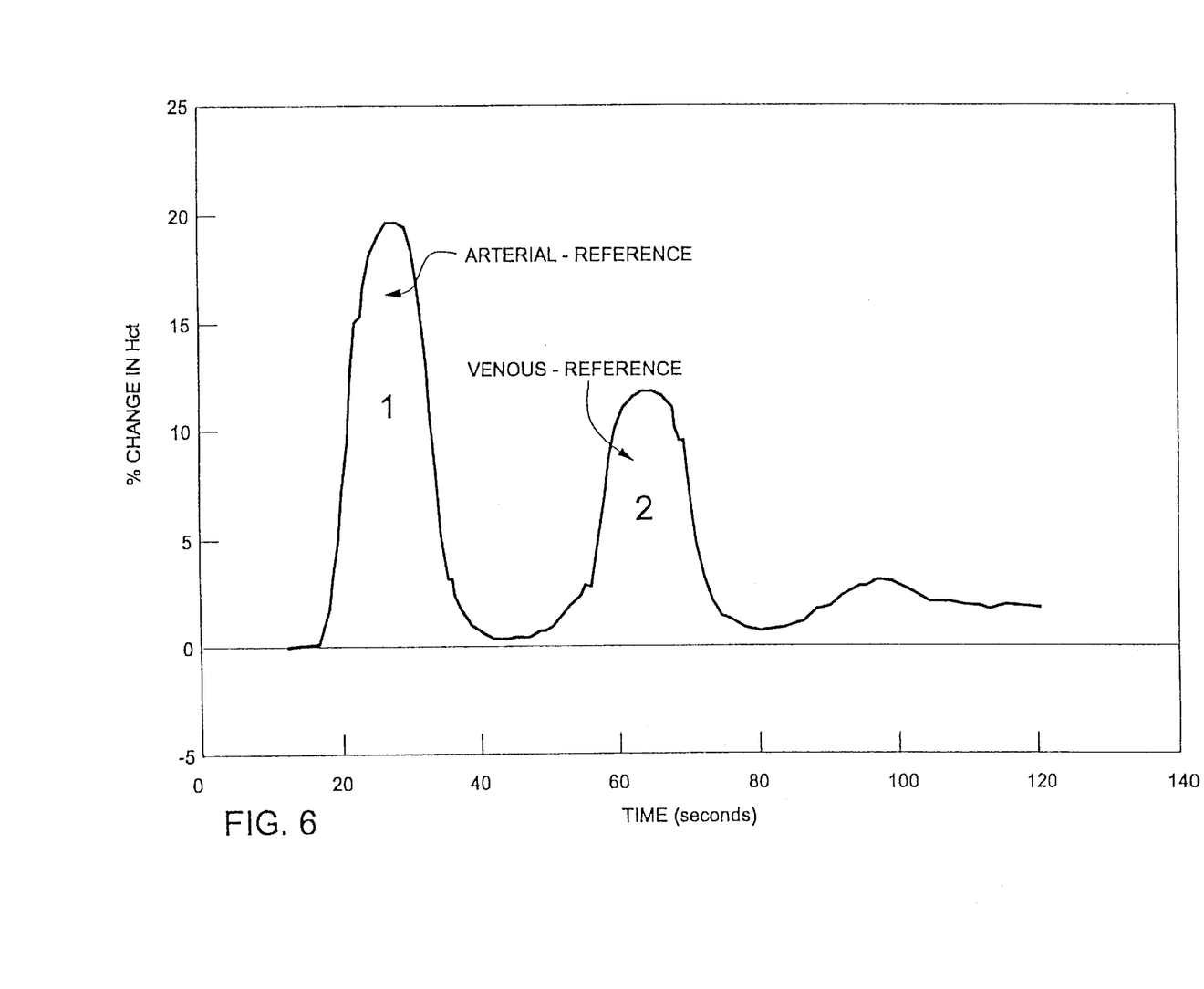
FIG. 6 represents a hematocrit dilution curve, due to saline injection.

In a further aspect of the present invention, a technique is provided to measure a patient's cardiac output. In this technique, two different volumes of saline, for example, 10 ml (arterial—"reference bolus") and 50 ml (venous—"measuring bolus"), are injected into arterial and venous tubing lines, respectively. As in FIG. 6, the reference bolus may be injected at zero time and the measuring bolus may be injected about 40 seconds later. However, the times of injection are adjustable. By calculating the area under the curves 1 and 2 as seen in FIG. 6 and by knowing the blood flow rate, Q, in the extracorporeal circuit, the cardiac output (C.O.) can be computed as:

$$\text{C.O.} = (50 \text{ ml}/10 \text{ ml})(\int (10 \text{ ml bolus})dt/\int (50 \text{ ml bolus})dt)Q \tag{6}$$

where: Q=blood flow rate of pump and ∫(50 ml bolus) dt=area under curve 2 and ∫(10 ml bolus) dt=area under curve 1.

Once the cardiac output is determined, the oxygen consumption rate can be measured. Assuming the oxygen saturation on the arterial side of the oxygenator to be 100%, measuring the oxygen saturation values on the venous side of the oxygenator, and measuring the hematocrit value and the cardiac output, the instantaneous value for the oxygen consumption rate, $dO_2/dt$, is derived as:

$$dO_2/dt=(C.O.)(Hct)(13.8/3.0)(S_aO_2 - S_vO_2) \quad (7)$$

where: C.O.=cardiac output

Hct=hematocrit $S_aO_2$ =arterial oxygen saturation=100%

$S_vO_2$ =venous oxygen saturation

Thus, the present invention also enables the determination of the oxygen consumption rate.

The present invention further provides a new apparatus and a new method for the continuous monitoring of the quantity, size, and concentration of microemboli (platelet aggregates, clots, air bubbles, etc.) in the blood.

Figure 7A:
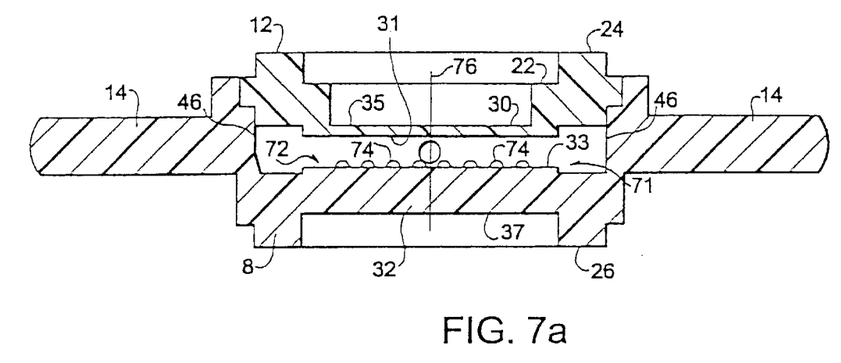
FIGS. 7a and 7b show two embodiments for the improved disposable blood circuit with a multiple, mini-lensing, linear array.

FIG. 7a shows the disposable conduit 10 with a multiple, mini-lens, linear array 72. This mini-lens array method allows for a narrow optical field of view and, hence, aggregate sizing.

The mini-lens array is located at the midline 71 which is defined by the cut-line 4—4 through FIG. 3. The midline 71 is transverse to the direction of blood flow. In FIG. 7a, the direction of blood flow is out of the paper. A group of spaced hemispheric lenses 74 are positioned along the midline 71 on the inner surface 33 of wall 32. In a preferred embodiment there are 8 lenses, each having a radius of 1 mm. Each lens 74 is spaced 2 mm from the adjacent lens. The two centrally located lenses are each 1 mm from the vertical center line 76. The mini-lens array acts as a "focusing bubble" on both sides of the disposable detection area, where the LED light source arrays (660 nm, 810 nm, 1300 nm) from the photoemitter 102 are focused by these mini-lenses or "bubbles" onto an array of detectors found in photodetector 104. By strobing and focusing the LED light sources independently, only a narrow section of the blood conduit is optically viewed with each wavelength individually. Therefore, when a blood embolus (platelet aggregate or clot) passes into that narrow region of illumination, a light transmission difference is sensed and the size of the embolus can be quantified. Noting the background or baseline (normal) scattering characteristics of the blood medium, when clots (or emboli) form, different absorption and scattering values are detected as "spikes." A digital signal processing algorithm is performed wherein the amplitude of the "spikes" above the baseline are counted as aggregates of a certain diameter (see FIG. 8). The number of "spikes" per unit time relate to the concentration (and quantity) and the width of the "spikes" relate to the aggregate sizes. In a preferred embodiment, the mini-lenses may be used in combination with a pedestal.

Figure 7B:
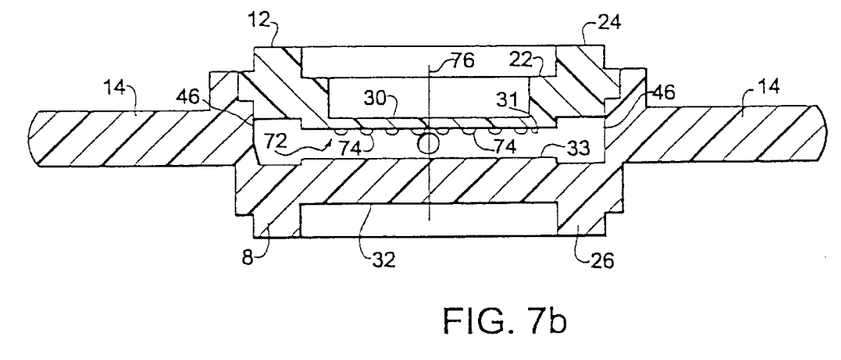
Figure 8:
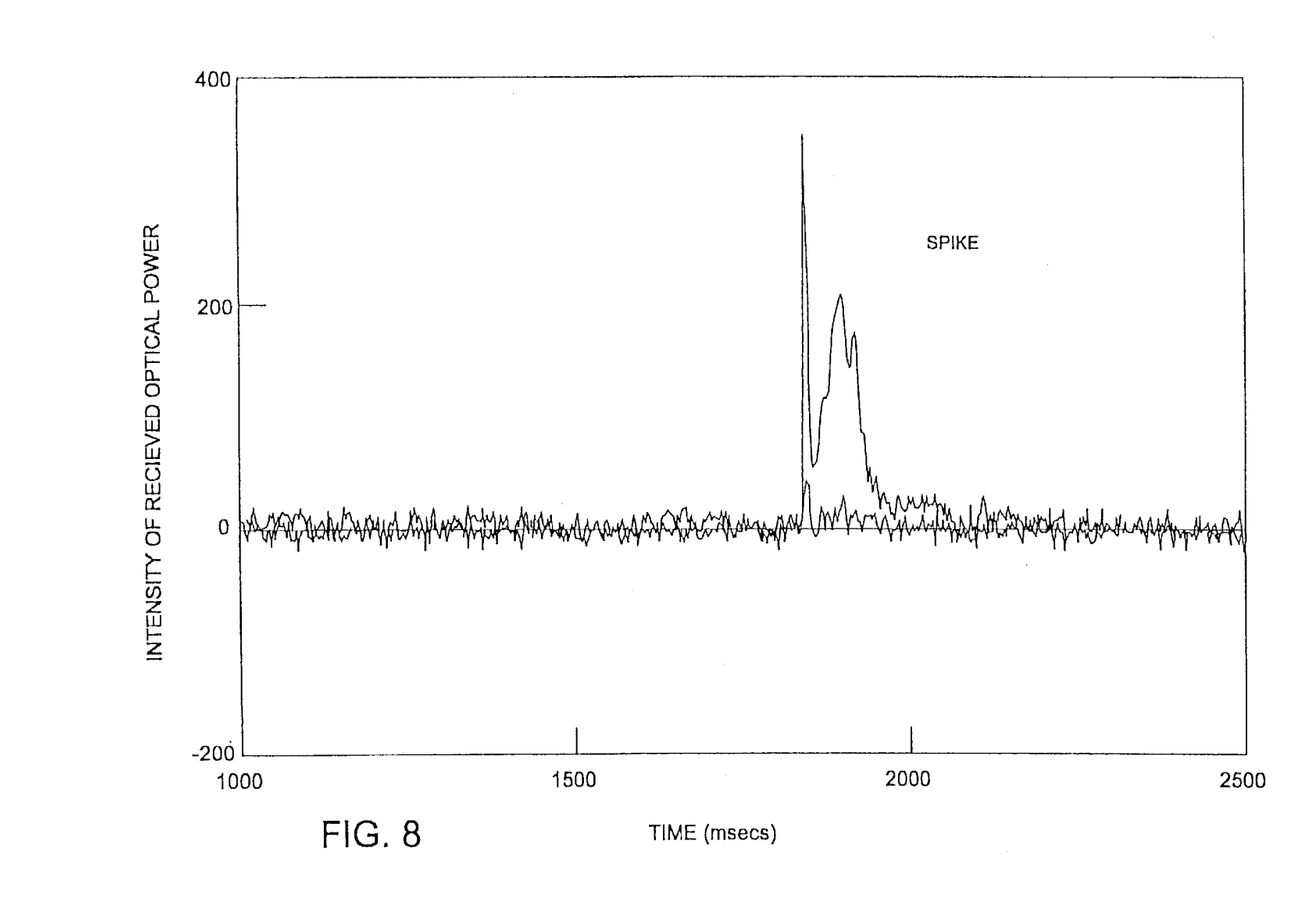
FIG. 8 shows the electronic signal representing the baseline photo-electric noise due to the scattering of photons in a turbid medial such as blood.

FIG. 7b shows an alternative embodiment of the mini-lens array where like reference numerals denote like elements to the mini-lens array in FIG. 7a. In the embodiment of FIG. 7b, however, the lenses 74 are located along the inner surface 31 of wall 30. In this arrangement, the photoemitter 104 shines radiant energy through the blood sample onto the mini-lens array. A series of detectors in the photodetector 104 are associated with each of the lenses 74 to detect presence of an embolus.

The described embodiments are to be considered in all respects only as illustrative and not restrictive. The present invention may be embodied in other specific forms without departing from its intent or essential characteristics.

What is claimed is:

1. A noninvasive method of measuring cardiac output in a dialysis system having arterial and venous tubing lines using a first extracorporeal cuvette located at an input to a dialyzer in said dialysis system and a second extracorporeal cuvette located at an output of said dialyzer, each extracorporeal cuvette having an inlet, an outlet, and a conduit in fluid communication therebetween, said conduit having first and second opposed walls allowing electromagnetic radiation therethrough with inner surfaces thereof having a first predetermined separation therebetween, outer surfaces and said inner surfaces of said first and second opposed walls being planar, said inner surface of said first wall including a pedestal emanating outwardly toward the inner surface of said second wall, said pedestal having a planar end surface defining a second predetermined separation from said second wall, said first predetermined separation being greater than said second predetermined separation so that a shorter radiation path length is created across said second predetermined separation, said method comprising the steps of:

injecting a first saline bolus into the arterial tubing;

injecting a second saline bolus into the venous tubing;

determining the blood flow rate through at least one of said extracorporeal cuvettes in the dialysis system;

selecting the first saline bolus as a reference bolus and the second saline bolus as a measuring bolus;

determining a first ratio of the measuring bolus to the reference bolus;

determining the change of hematocrit over time for the reference bolus by comparing an output of said first extracorporeal cuvette with an output of said second extracorporeal cuvette;

determining the change of hematocrit over time for the measuring bolus by comparing an output of said first extracorporeal cuvette with an output of said second extracorporeal cuvette;

determining a second ratio of the reference bolus over time to the measuring bolus over time; and calculating the product of the first ratio, the second ratio and the blood flow rate.

2. A method for detecting blood emboli using an extracorporeal cuvette having an inlet, an outlet, and a conduit in fluid communication therebetween, said conduit having first and second opposed walls with inner surfaces thereof having a first predetermined separation therebetween, said method comprising the steps of:

allowing blood to flow from said inlet to said outlet through said conduit;

emitting, with an emitter on an outer surface of said first wall, radiation through said first wall into the blood flow in said conduit;

receiving, with a sensor on an outer surface of said second wall, radiation passing through the blood flow in said conduit;

defining, with a plurality of lenses arranged along the surface of said second wall, a region of illumination to focus the radiation from the emitter and received by said sensor; and detecting, by said sensor, a change in radiation when a blood embolus passes through said region of illumination, said change in radiation indicating a number and size of blood emboli.

3. The method as set forth in claim 2, wherein said emitter is a photoemitter and said plurality of lenses act to strobe and focus a plurality of LED light sources in said photoemitter independently such that only a narrow section of the conduit is optically viewed for any given wavelength of said LED light sources.

4. A method for monitoring blood constituents using an extracorporeal cuvette having an inlet, an outlet, and a conduit in fluid communication therebetween, said conduit having first and second opposed walls allowing electromagnetic radiation therethrough with inner surfaces thereof having a first predetermined separation therebetween, outer surfaces and said inner surfaces of said first and second opposed walls being planar, said inner surface of said first wall including a pedestal emanating outwardly toward the inner surface of said second wall, said pedestal having a planar end surface defining a second predetermined separation from said second wall, said first predetermined separation being greater than said second predetermined separation, said method comprising the steps of:

allowing blood to flow from said inlet to said outlet through said conduit;

emitting, with an emitter on an outer surface of said first wall, radiation through said first wall into the blood flow in said conduit, a path length of said radiation corresponding to said second predetermined separation between the planar end surface of said pedestal and said inner surface of said second wall; and receiving, with a sensor on an outer surface of said second wall, radiation passing through the blood flow in said conduit across the radiation path length, the first wall, the second wall and the pedestal.

* * * * *